United States Patent [19]

Diderichsen et al.

[11] Patent Number: 5,234,823
[45] Date of Patent: Aug. 10, 1993

[54] CHIMERIC ENZYMES

[75] Inventors: Borge K. Diderichsen, Hellerup; Helle Outtrup, Ballerup; Martin Shulein, Kobenhav; Barrie E. Norman, Farum, all of Denmark

[73] Assignee: Novo Industri A/S, Bagsvaerd, Denmark

[21] Appl. No.: 607,798

[22] Filed: Oct. 26, 1990

Related U.S. Application Data

[63] Continuation of Ser. No. 67,992, Jun. 29, 1987, abandoned.

[30] Foreign Application Priority Data

Jun. 30, 1986 [DK] Denmark .............................. 3111/86

[51] Int. Cl.$^5$ .......................... C12D 19/14; C12N 9/28
[52] U.S. Cl. ..................................... 435/99; 435/202; 935/47
[58] Field of Search ................. 435/202, 205, 210, 99, 435/98, 96; 935/47

[56] References Cited

FOREIGN PATENT DOCUMENTS

| 82302001.1 | 4/1981 | European Pat. Off. . |
|---|---|---|
| 85114004.6 | 5/1986 | European Pat. Off. . |
| 86305057.1 | 1/1987 | European Pat. Off. . |
| PCT/NL84/-00021 | 1/1985 | PCT Int'l Appl. . |

OTHER PUBLICATIONS

Sibakov, M., (1986), Eur. J. Biochem., 155, 527–581.
Gray, G. L., et al., (1986), J. Bacteriol., 166(2), 635–643.
Yuuki, T., et al., (1985), J. Biochem., 98, 1147–1156.
Ihara et al., J. Biochem., 1985, 98:95–103.
Welker and Campbell, 1967, J. Bacteriol., 94:1124–1130.
Kuhn et al., 1982, J. Bacteriol., 149:372–373.
Palva, 1982, Gene, 19:81–87.
Ortlepp et al., 1983, Gene, 23:267–276.
Takkinen et al., 1983, J. Biol. Chem., 258:1007–1013.
Stephens et al., 1984, J. Bacteriol., 158:369–372.

*Primary Examiner*—Charles L. Patterson, Jr.
*Attorney, Agent, or Firm*—Pennie & Edmonds

[57] ABSTRACT

Chimeric alpha-amylases are disclosed of the formula $$Q-R-L$$

in which Q is a N-terminal polypeptide residue of from 55 to 60 amino acid residues which is at least 75 percent homologous to the 55 N-terminal amino acid residues in the *Bacillus amyloliquefaciens* alpha-amylase as described in Takkinen et al., J. Biol. Chem. 258 (1983) 1007–1013, R is a polypeptide residue of the general formula Pro—Tyr—Asp—Leu—Tyr—Asp—Leu—Gly—Glu—

Phe—$X_8$—Gln—Lys—Gly—Thr—Val—Arg—Thr—

Lys—Tyr—Gly—Thr—Lys—$X_9$—Glu—Leu—Gln—

$X_{10}$—Ala—Ile—Lys.

L comprises a C-terminal polypeptide of from 390 to 400 amino acid residues which is at least 75 percent hololgous to the 395 C-terminal amino acid residues in the *Bacillus licheniformis* 584 (ATCC 27811) alpha-amylase.

10 Claims, 6 Drawing Sheets

B. LICHENIFORMIS

B. AMYLOLIQUEFACIENS

```
1
Val Asn Gly Thr Leu Met Gln Tyr Phe Glu Trp Tyr Thr Pro Asn Asp Gly Gln His Trp
GTA AAT GGC ACG CTG ATG CAG TAT TTT GAA TGG TAT ACG CCG AAC GAC GGC CAG CAT TGG
                                                                              20

Lys Arg Leu Gln Asn Asp Ala Glu His Leu Ser Asp Ile Gly Ile Thr Ala Val Trp Ile
AAA CGA TTG CAG AAT GAT GCG GAA CAT TTA TCG GAT ATC GGA ATC ACT GCC GTC TGG ATT
                                                                              40

Pro Pro Ala Tyr Lys Gly Leu Ser Gln Ser Asp Asn Gly Tyr Gly
CCT CCC GCA TAC AAA GGA TTG AGC CAA TCC GAT AAC GGA TAC GGA
                                    55
```

FIG.5

CHIMERIC ENZYMES

This is a continuation of application Ser. No. 07/067,992, filed June 29, 1987, abandoned.

TABLE OF CONTENTS

1. Field of the Invention
2. Background of the Invention
3. Summary of the Invention
   3.1 Definitions
4. Brief Description of the Drawings
5. Detailed Description of the Invention
   5.1 Amino Acid Sequences of Preferred Embodiments
   5.2 Methods for Producing the Chimeric Amylases
   5.3 Uses of the Chimeric Amylases
6. Example: Chimeric Amylase QL1864
   6.1 Construction of Hybrid QL1864
   6.2 Analysis of Chimerio Amylase Produced by QL1864
      6.2.1. Saccharification Test For Chimeric Amylase
      6.2.2. Thermoactivation of Chimeric Amylase
      6.2.3. Stability of Chimeric Amylase

1. FIELD OF THE INVENTION

This invention relates to starch hydrolysing enzymes. More specifically, the present invention is directed to chimeric alpha-amylases, to processes for preparing such chimeric alpha-amylases and to the use thereof for the overall enzymatic conversion of starch into high DX syrups, the term DX meaning percentage by weight of dextrose (D-glucose) calculated on the basis of dry substance (DS) of the syrup.

2. BACKGROUND OF THE INVENTION

The overall enzymatic process generally adopted by manufacturers of high DX syrups from starch entails two-stages: liquefaction and saccharifications. The first step, the liquefaction, involves the hydrolysis of starch into a mixture of oligosaccharides, the so called maltodextrins. This process is catalyzed by alpha-amylases at a temperature of at least 75 C, preferably at about 90° C. or by a jet-cooking process wherein the starch slurry is heated for at least several minutes to 105°–110° C., usually with a single dose of alpha-amylase, and then held at about 90° C. for at least one hour.

A variety of microbial, particularly bacterial, alpha-amylases are commercially available for the liquefaction process, for example BAN TM (from *Bacillus amyloliquefaciens* and TERMAMYL ® (from *Bacillus icheniformis*), both supplied by NOVO INDUSTRI A/S, Denmark, and THERMOLASE TM (from *Bacillus stearothermophilus*) available from Enzyme Development Corporation, N.Y., U.S.A. While BAN alpha-amylase is only stable up to about 85° C. and hence barely suitable for the jet-cooking process, both the TERMAMYL and THERMOLASE enzymes are well adapted for this almost globally preferred mode of starch liquefaction because they are heat stable.

The saccharification step, in which the maltodextrins are converted into dextrose, is mostly catalyzed by a glucoamylase enzyme. Commercial glucoamylase preparations, usually derived from *Aspergillus* or *Rhizopus* species, are available from various manufacturers, e.g. as AMG TM 200L, a product obtained from *Aspergillus niger* and manufactured by NOVO INDUSTRI A/S, Denmark.

With a view to further increasing the dextrose yield from 30–40 percent by weight DS maltodextrin solutions it has become customary to conduct the saccharification process with glucoamylase in the presence of a debranching enzyme in order to facilitate the hydrolysis of branched oligosaccharides originating from the amylopectin portion of starch. One such debranching enzyme with maximum activity in the same pH and temperature ranges as glucoamylase is disclosed in European Patent Application No. 82302001.1 (Publication No. 0063909). The debranching enzyme is marketed by NOVO INDUSTRI A/S, Denmark, either as such under the proprietary name, PROMOZYME, or as a composition with suitable admixture of glucoamylase under the proprietary name DEXTROZYME.

Unfortunately, the otherwise very favorable combination of *B. licheniformis* alpha-amylase for liquefaction and glucoamylase-PROMOZYME for saccharification in the conversion of starch to high DX syrups entails an inconvenience. It has been observed that the presence of residual alpha-amylase activity from the liquefaction stage has a negative effect on the maximum DX obtainable by saccharification with glycoamylase-PROMOZYME. The problem is greatest with the thermostable *B. licheniformis* alpha-amylase which is still active at the preferred conditions for saccharification (of about pH 4.6 and temperature of about 60° C., respectively). A remedy has been devised consisting of inactivation of the alpha-amylase prior to saccharification by acidification of the liquefied starch to a pH below 4.5 while maintaining a temperature of at least 90° C. Following inactivation of the alpha-amylase, the temperature and pH are adjusted to saccharification conditions, meaning that the pH has to be brought up to about 4.5. This additional pH adjustment inevitably increases the salt content of the syrup and hence the expenses connected with de-salting the final syrup.

The object of the present invention is to overcome the above-mentioned inconveniences still associated with the use of *B. licheniformis* alpha-amylase for the conversion of starch into a high DX syrup. This and other objects which will be dealt with subsequently in this specification are attained by conducting the liquefaction process with a novel type of alpha-amylase.

3. SUMMARY OF THE INVENTION

The chimeric alpha-amylase enzymes of the invention comprise all or portions of the amino terminus of the alpha-amylase derived from *B. amyloliquefaciens* joined to the carboxy terminus of the alpha-amylase derived from *B. licheniformis*. Briefly stated, the present invention provides chimeric alpha-amylases of the general formula I

Q—R—L  (I)

in which Q is a N-terminal polypeptide of from 55 to 60 amino acid residues which is at least 75 percent, preferably at least 80 percent, and more preferably at least 90 percent homologous to the 55 N-terminal amino acid residues in the *Bacillus amyloliquefaciens* alpha-amylas (Takkinen, et al., 1983, J. Biol. Chem 258:1007–1013;

R is a polypeptide of the general formula Ia: (Ia)

Pro—Tyr—Asp—Leu—Tyr—Asp—Leu—Gly—Glu—Phe—$X_8$—Gln—Lys—Gly—Thr—Val—  (Ia)

Arg—Thr—Lys—Tyr—Gly—Thr—Lys—$X_9$—Glu—Leu—Gln—$X_{10}$—Ala—Ile—Lys in which
$X_8$ is His or Gln,
$X_9$ is Gly or Ser,
$X_{10}$ is Ser or Asp; and
L is a C-terminal polypeptide of from 390 to 400 amino acid residues which is at least 75 percent, preferably at least 80 percent, and more preferably at least 90 percent homologous to the 395 C-terminal amino acid residues in the *Bacillus licheniformis* 584 (ATCC 27811) alpha-amylase
(Stephens et al., 1984, J.Bacteriol, 158:369–372) as represented by form IC, *infra*.

Because of the relevance of Takkinen et al., *supra*, and Stephens et al., *supra*, in defining the amino id sequences of the alpha amylases produced by B. *amyloliquefaciens* and B. *licheniformis*, portions of which sequences are contained within the chimeric amylases of the invention, these references are incorporated by reference herein in their entirety.

The amino acid sequence of the chimeric enzymes described and shown above may be modified by the substitution, deletion or addition of amino acid residues within the sequence which result in a silent change in the molecule so that the product retains its activity. Such amino acid substitutions may be made on the basis of similarity in polarity, charge, solubility, hydrophobicity, hydrophilicity and/or the amphipathic nature of the residues involved. For example, acidic amino acids (negatively charged at pH 6.0) include aspartic acid and glutamic acid; basic amino acids (positively charged at pH 6.0) include lysine and arginine; amino acids with uncharged polar head groups or nonpolar head groups having similar hydrophilic properties include the following: leucine, isoleucine, valine; glycine, alanine; asparagine, glutamine; serine, threonine; phenylalanine, tyrosine.

In another aspect the invention relates to processes for the production of the novel amylase of the first aspect above. According to this second aspect the amylases of the invention may be produced by the use of conventional genetic engineering techniques, such as gene splicing or by use of in vivo recombination to be described below, or by chemical synthetic techniques.

In a third aspect the invention relates to the use of the chimeric amylases in the liquefaction stage in the production of high DX syrups, especially in the jet cooking process mentioned above.

The chimeric alpha-amylases upon which the invention is based surprisingly demonstrate the excellent thermostability characteristics of alpha-amylase derived from B. *licheniformis*, but at the same time a reduced negative effect on the maximum obtainable DX without being inactivated prior to the saccharification step. The invention is demonstrated herein, by way of examples, in which a segment of B. *licheniformis* alpha-amylase consisting of from about amino acid residue number 57 to about amino acid residue number 87, calculated from the N-terminal end of B. *licheniformis* alpha-amylase or, alternatively, the whole N-terminal segment thereof, is exchanged with the corresponding segment of B. *amyloliquefaciens* alpha-amylase. The residual activity of the chimeric alpha-amylase has at the most a negligible negative effect on the maximum DX obtainable by saccharification with glucoamylase-PROMOZYME while still retaining the excellent thermostability characteristic of B. licheniformis alpha-amylase.

3.1 DEFINITIONS

As used herein, the following terms shall have the meanings indicated:
DS=dry substance
DX=percentage by weight of dextrose (D-glucose).
$DP_n$=an oligosaccharide comprising n D-glucose units joined by phosphate linkages.

4. BRIEF DESCRIPTION OF THE DRAWINGS

The invention will be described in further detail in the following specification and examples with reference to the appended drawing in which.

Figure 1A:
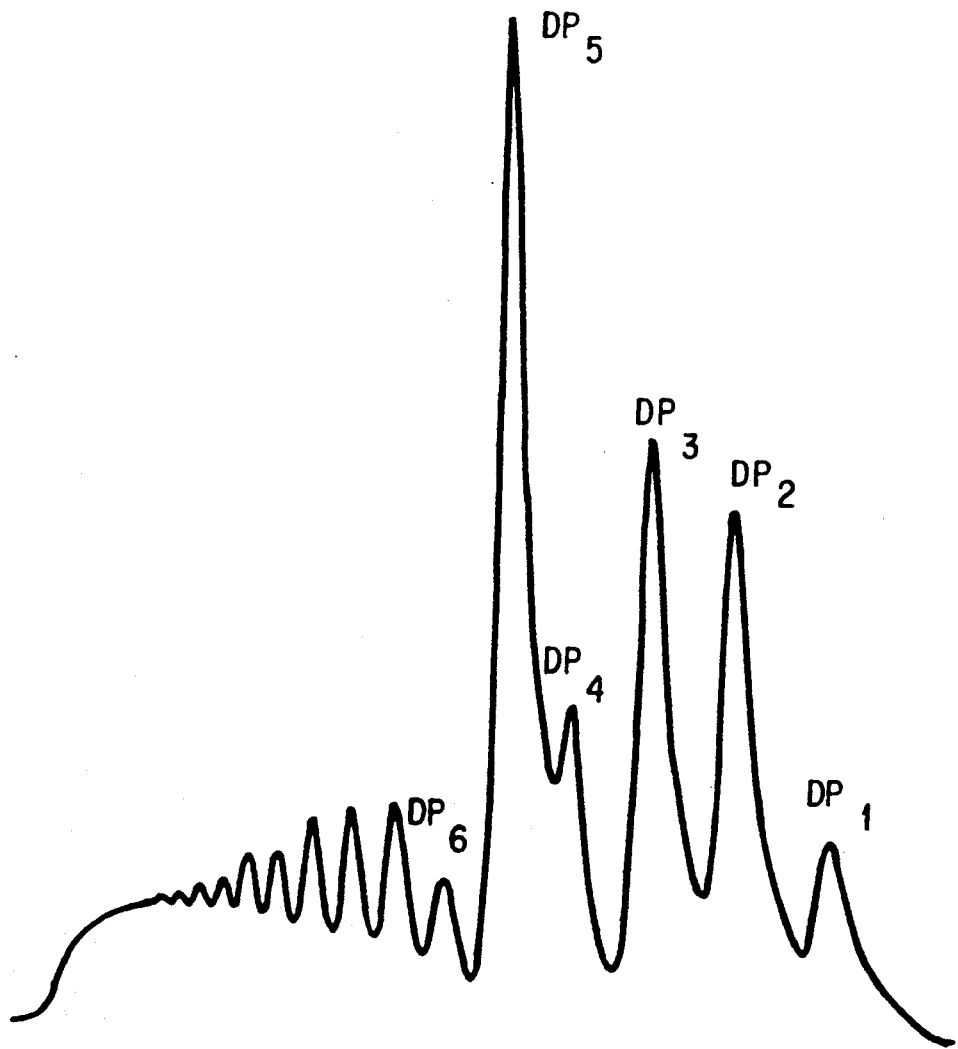
FIG. 1 shows gel-permeation chromatograms of alpha-amylases from B. *licheniformis*, B. *amyloliquefaciens* and an alpha-amylase according to the invention.

FIG. 5 shows the amino acid sequence of the 57 N-terminal amino acids of *Bacillus amyloliquefaciens* alpha-amylase, as published in Takkinen, et al., 1983, J. Biol. Chem. 258:1007–1013.

5. DETAILED DESCRIPTION OF THE INVENTION

As indicated above the invention relates to chimeric alpha-amylases of the general formula I $$Q—R—L \qquad (I)$$

in which Q, R, and L are defined as described in Section 3 supra. Preferred formulas are described in the subsections below.

5.1 Amino Acid Sequences of Preferred Embodiments

A preferred alpha-amylase of the general formula I is one in which Q is an N-terminal polypeptide residue of the general formula Ib:

$X_1$—Asn—Gly—Thr—Leu—Met—Gln—Tyr—Phe—Glu—Trp—Tyr—$X_2$—Pro—Asn—Asp— (Ib)

Gly—Gln—His—Trp—Lys—Arg—Leu—Gln—Asn—Asp—$X_3$—Leu—$X_4$—Gly—Ile—Thr—

Ala—Val—Trp—Ile—Pro—Pro—Ala—Tyr—Lys—Gly—$X_5$—Ser—Gln—$X_6$—Asp—$X_7$—

Gly—Tyr—Gly in which
$X_1$ is Ala-Asn-Leu or Val,
$X_2$ is Met or Thr,
$X_3$ is Ser-Ala-Tyr or Ala-Glu-His,
$X_4$ is Ala-Glu-His or Ser-Asp-Ile,
$X_5$ is Thr or Leu, $X_6$ is Ala or Ser,
$X_7$ is Val or Asn; and
R and L are defined as previously in Section 3 supra.

In another preferred alpha-amylase of the general formula I, Q and R are defined as previously described, and L is a C-terminal polypeptide residue of the general formula Ic Ser—Leu—His—Ser—Arg—Asp—Ile—Asn—Val—Tyr—Gly—Asp—Val— (Ic)

Val—Ile—Asn—His—Lys—Gly—Gly—Ala—Asp—Ala—Thr—Glu—Asp—Val—Thr—

Ala—Val—Glu—Val—Asp—Pro—Ala—Asp—Arg—Asn—Arg—Val—Ile—Ser—Gly—

Glu—His—Arg—Ile—Lys—Ala—Trp—Thr—His—Phe—His—Phe—Pro—Gly—Arg—

Gly—Ser—Thr—Tyr—Ser—Asp—Phe—Lys—Trp—His—Trp—Tyr—His—Phe—Asp—

Gly—Thr—Asp—Trp—Asp—Glu—Ser—Arg—Lys—Leu—Asn—Arg—Ile—Tyr—Lys—

Phe—Gln—Gly—Lys—Ala—Trp—Asp—Trp—Glu—Val—Ser—Asn—Glu—Asn—Gly—

Asn—Tyr—Asp—Tyr—Leu—Met—Tyr—Ala—Asp—Ile—Asp—Tyr—Asp—His—Pro—

Asp—Val—Ala—Ala—Glu—Ile—Lys—Arg—Trp—Gly—Thr—Trp—Tyr—Ala—Asn—

Glu—Leu—Gln—Leu—Asp—Gly—Phe—Arg—Leu—Asp—Ala—Val—Lys—His—Ile—

Lys—Phe—Ser—Phe—Leu—Arg—Asp—Trp—Val—Asn—His—Val—Arg—Glu—Lys—

Thr—Gly—Lys—Glu—Met—Phe—Thr—Val—Ala—Glu—Tyr—Trp—Gln—Asn—Asp—

Leu—Gly—Ala—Leu—Glu—Asn—Tyr—Leu—Asn—Lys—Thr—Asn—Phe—Asn—His—

Ser—Val—Phe—Asp—Val—Pro—Leu—His—Tyr—Gln—Phe—His—Ala—Ala—Ser—

Thr—Gln—Gly—Gly—Gly—Tyr—Asp—Met—Arg—Lys—Leu—Leu—Asn—Ser—Thr—

Val—Val—Ser—Lys—His—Pro—Leu—Lys—Ala—Val—Thr—Phe—Val—Asp—Asn—

His—Asp—Thr—Gln—Pro—Gly—Gln—Ser—Leu—Glu—Ser—Thr—Val—Gln—Thr—

Trp—Phe—Lys—Pro—Leu—Ala—Tyr—Ala—Phe—Ile—Leu—Thr—Arg—Glu—Ser—

Gly—Tyr—Pro—Gln—Val—Phe—Tyr—Gly—Asp—Met—Tyr—Gly—Thr—Lys—Gly—

Asp—Ser—Gln—Arg—Glu—Ile—Pro—Ala—Leu—Lys—His—Lys—Ile—Glu—Pro—

Ile—Leu—Lys—Ala—Arg—Lys—Gln—Tyr—Ala—Tyr—Gly—Ala—Gln—His—Asp—

Tyr—Phe—Asp—His—His—Asp—Ile—Val—Gly—Trp—Thr—Arg—Glu—Gly—Asp—

Ser—Ser—Val—Ala—Asn—Ser—Gly—Leu—Ala—Ala—Leu—Ile—Thr—Asp—Gly—

Pro—Gly—Gly—Ala—Lys—Arg—Met—Tyr—Val—Gly—Arg—Gln—Asn—Ala—Gly—

Glu—Thr—Trp—His—Asp—Ile—Thr—Gly—Asn—Arg—Ser—Glu—Pro—Val—Val—

Ile—Asn—Ser—Glu—Gly—Trp—Gly—Glu—Phe—His—Val—Asn—Gly—Gly—Ser—

Val—Ser—Ile—Tyr—Val—Gln—Arg

In still another preferred alpha-amylase of the general formula I, Q has the general formula Ib and L is a C-terminal polypeptide residue of the general formula Ic, in which $X_1$ is Val, $X_2$ is Thr, $X_3$ is Ala-Glu-His, $X_4$ is Ser-Asp-Ile, $X_5$ is Leu, $X_6$ is Ser, and $X_7$ is Asn.

In yet another preferred alpha-amylase of the general formula I, Q has the general formula Ib in which $X_1$ is Val, $X_2$ is Thr, $X_3$ is Ala-Glu-His, $X_4$ is Ser-Asp-Ile, $X_5$ is Leu, $X_6$ is Ser, and $X_7$ is Asn; L is a C-terminal peptide residue of the general formula Ic; and amino acid residues $X_8$, $X_9$, and $X_{10}$ of R are Gln, Ser and Asp, respectively.

In yet another preferred alpha-amylase of the general formula I, Q has the general formula Ib in which Q, X1 is Val, $X_2$ is Thr, $X_3$ is Ala-Glu-His, $X_4$ is Ser-Asp-Ile, $X_5$ is Leu, $X_6$ is Ser, and $X_7$ is Asn; L is a C-terminal polypeptide residue of the general formula Ic; and amino acid residues $X_8$ $X_9$ and $X_{10}$ of R are His, Gly and Ser, respectively.

5.2 METHODS FOR PRODUCING THE CHIMERIC AMYLASES

The amylases of the invention are chimeric enzymes and may in accordance with the second aspect of the invention be produced in a number of ways as described below.

Naturally occurring enzymes may be genetically modified by random or site directed mutagenesis. Alternatively, part of one enzyme may be replaced by a part of another to obtain a chimeric enzyme. This replacement can be achieved either by conventional in vitro gene splicing techniques or by in vivo recombination or by combinations of both techniques. When using conventional in vitro gene splicing techniques, a desired portion of the alpha-amylase gene coding sequence may be deleted using appropriate site-specific restriction enzymes; the deleted portion of the coding sequence may then be replaced by the insertion of a desired portion of a different alpha-amylase coding sequence so that a chimeric nucleotide sequence encoding a new alpha-amylase is produced.

The in vivo recombinantion techniques depend on the fact that different DNA segments with highly homologous regions (identity of DNA sequence) may recombine, i.e. break and exchange DNA, and establish new bonds in the homologous regions. Accordingly, when the coding sequences for two different but homologous amylase enzymes are used to transform a host cell, recombination of homologous sequences in vivo will result in the production of chimeric gene sequences. Translation of these coding sequences by the host cell will result in production of a chimeric amylase gene product.

The alpha-amylase genes from *Bacillus licheniformis* (herein designated *amyL*) and from *Bacillus amyloliquefaciens* (herein designated *amyQ*) are approximately 70 percent homologous at the DNA level and suitable for hybrid formation by in vivo gene splicing.

In an alternate embodiment, the chimeric enzyme may be synthesized by standard chemical methods known in the art. For example, see Hunkapiller et al., 1984, Nature 310:105-111. Accordingly, peptides having the amino acid sequences described supra may be synthesized in whole or in part and joined to form the chimeric enzymes of the invention.

5 3 USES OF THE CHIMERIC AMYLASES

According to its third aspect the invention relates to the use of the novel alpha-amylases in the liquefaction stage in the overall enzymatic conversion of starch into high DX syrups.

As indicated previously residual activity from the use of the thermostable alpha-amylase from *B. licheniformis* in the liquefaction stage entails a negative effect on maximum obtainable D-glucose yield in the saccharification stage when using *A. niger* glucoamylase and *B. acidopullulyticus* pullulanase.

The reason for this negative effect is not fully understood, but it is assumed that *B. licheniformis* alpha-amylase generates "limit dextrins" which are poor substrates for *B. acidopullulyticus* pullulanase, by hydrolyzing 1, 4-alpha-glucosidic linkages close to the branchpoints in amylopectin. These limit dextrins which contain too few glucose units in one or more of the side chains will be less susceptible to *B. acidopullulyticus* pullulanase attack.

Figure 1B:
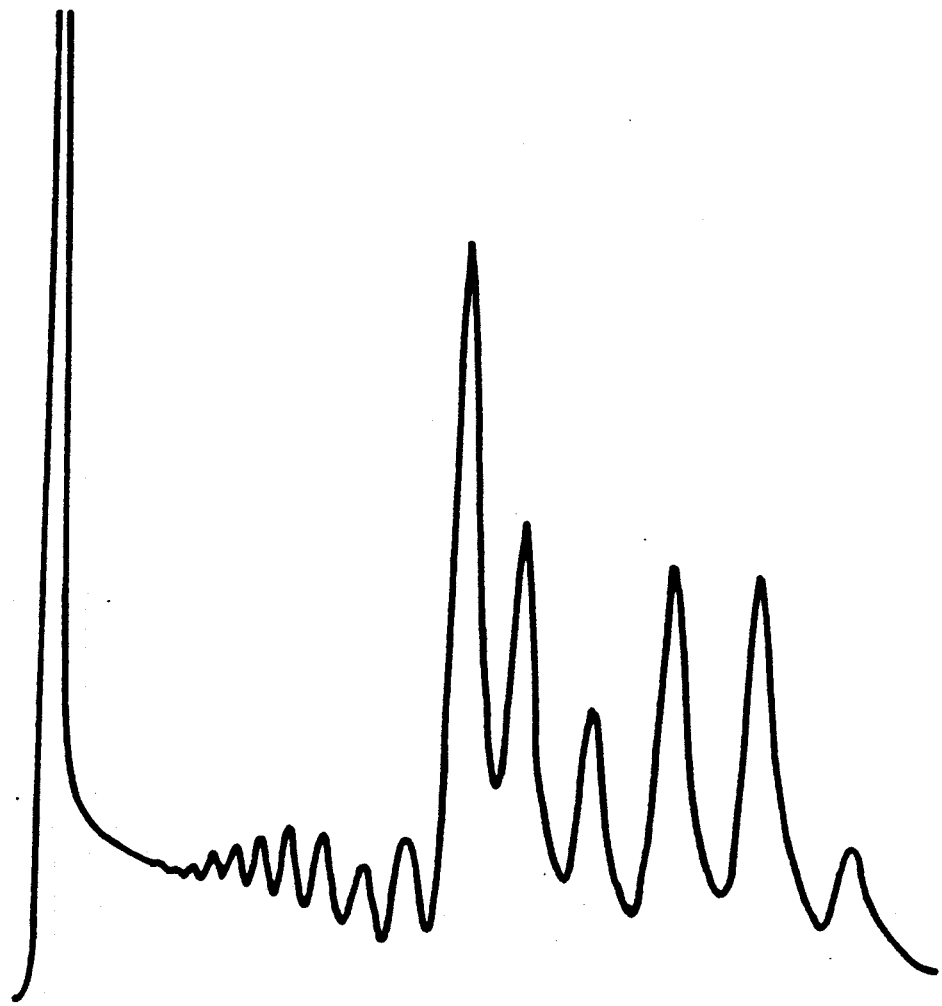
Figure 1C:
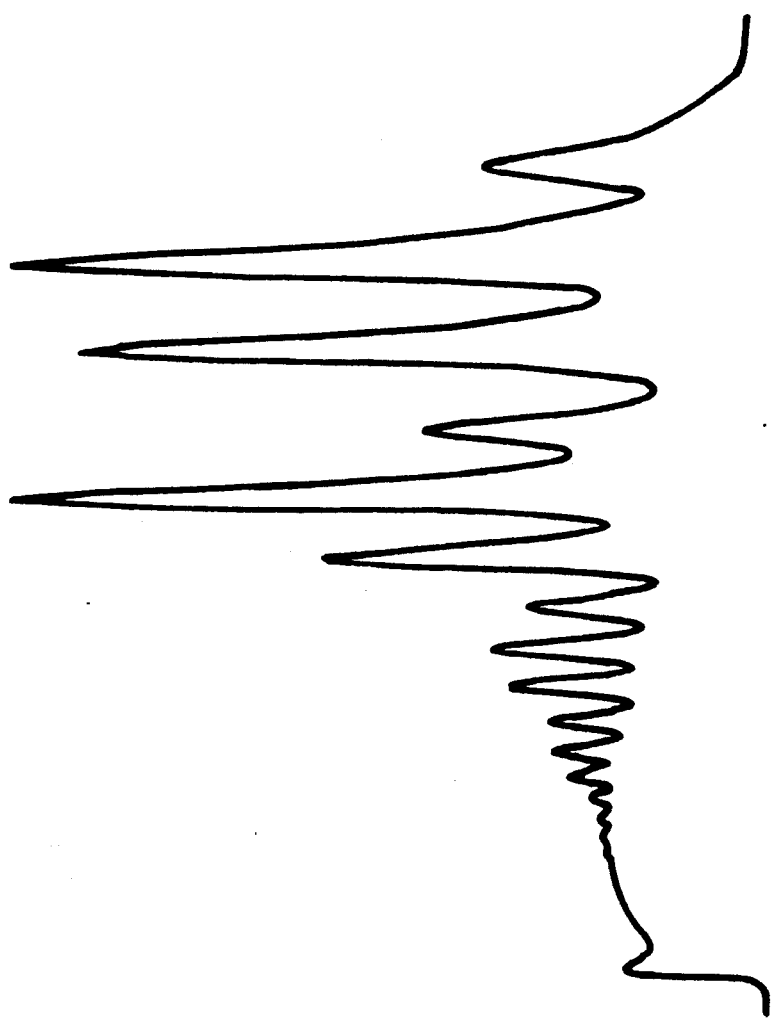

In FIG. 1 the action patterns for *B. licheniformis* alpha-amylase, *B. amyloliquefaciens* alpha-amylase, and the hybrid QL1864 alpha-amylase on amylopectin are indicated by the gel-permeation chromatograms taken from amylopectin digests after 48 hours.

From the FIGURE it is seen that the action pattern of *B. licheniformis* alpha-amylase on amylopectin is different from that of *B. amyloliquefaciens* alpha-amylase. The *B. licheniformis* enzyme produces mainly $DP_6$, $DP_5$ and $DP_3$ initially. On prolonged hydrolysis the $DP_6$ fraction is hydrolyzed further, and the major components are $DP_5$, $DP_3$, and $DP_2$. When *B. amyloliquefaciens* alpha-amylase is used the major components are $DP_6$.

The action pattern of the alpha-amylases of the invention as exemplified by the QL1864 alpha-amylase on amylopectin is distinctly different from both naturally occurring alpha-amylases, and as shown below, this changed action pattern surprisingly has resulted in the removal of the negative effect from *B. licheniformis* alpha-amylase on the D-glucose yield, while retaining the thermostability.

Accordingly it has been found that the alpha-amylases of the invention are very efficiently used for the liquefaction of starch.

6. EXAMPLE: CHIMERIC AMYLASE QL1864

The subsections below describe the production and characterization of the chimeric alpha-amylase QL1864.

6.1 Construction of Hybrid QL1864

Figure 2:
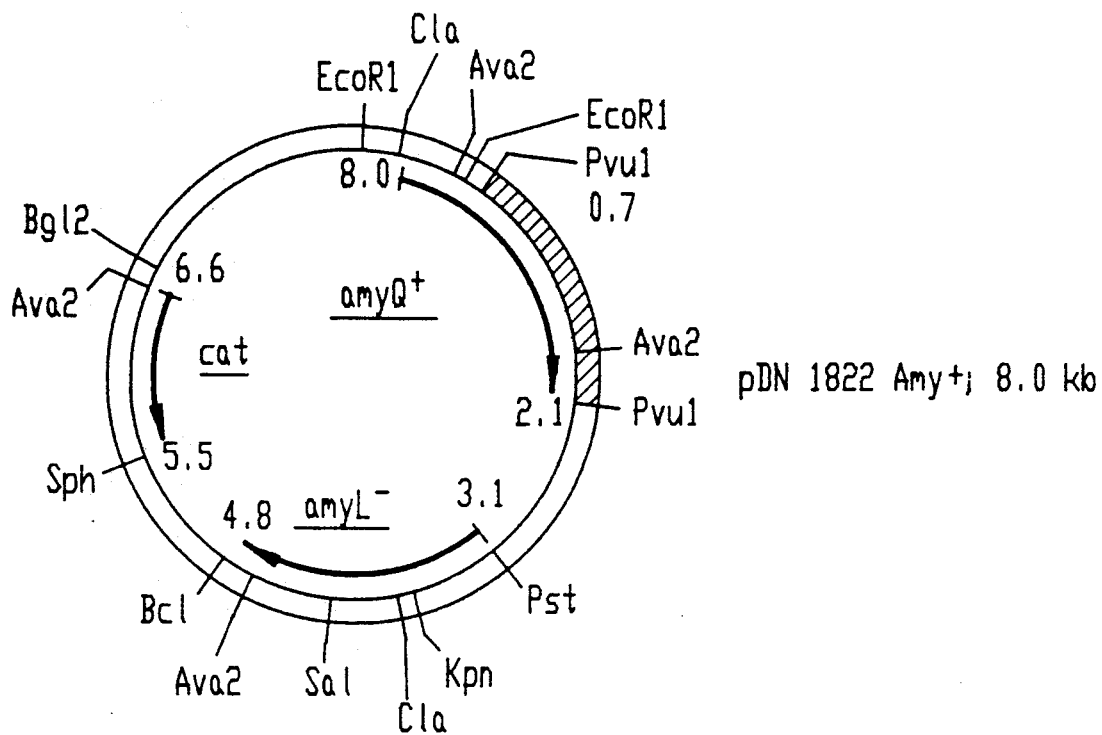
FIG. 2 shows the restriction map of plasmid pDN1822.
Figure 3:
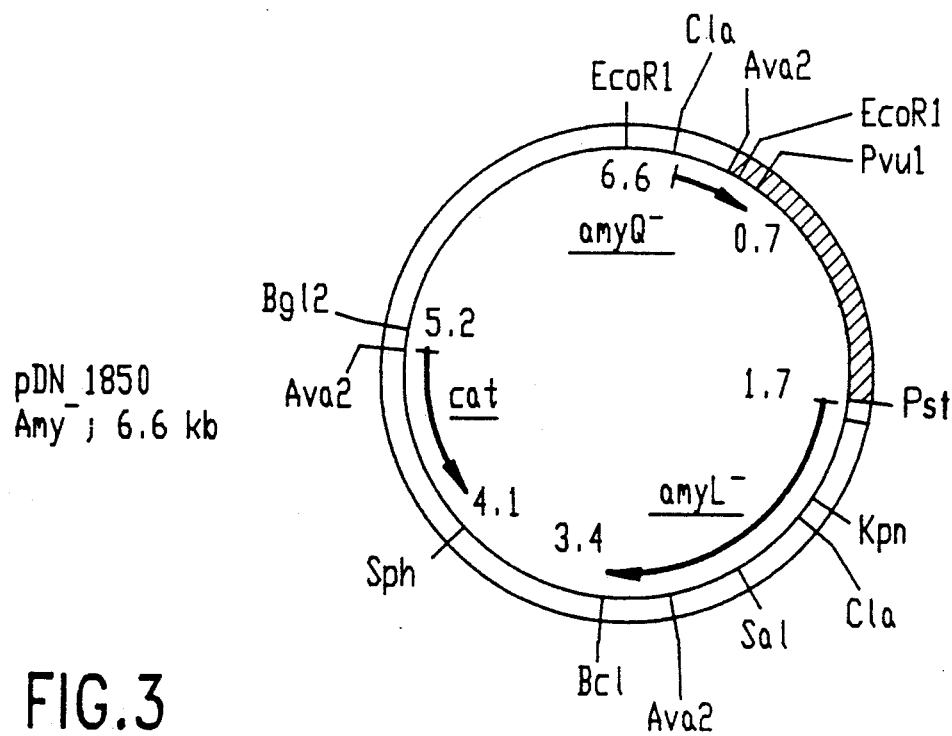
FIG. 3 shows the restriction map of plasmid pDN1850.

By conventional techniques, amyL and amyQ were cloned in *B. subtilis*. The restriction enzyme map of the two genes were in agreement with published DNA sequences for the genes for *B. licheniformis* amylase (amyL) (Stephens et al. 1984, J. Bacteriol. 158: 369) and *B. amyloliquefaciens* amylase (amyQ) (Takkinen et al., 1983, J. Biol. Chem 258:1007) 1983), respectively.

amyQ (amyQ+) and a C-terminal part of amyL (amyL-were placed in parallel on plasmid pDN1822. This is a *B. subtilis* plasmid derived from cloning vector pUB110 and harbouring the chloramphenicol resistance ($Cam^R$) gene (cat gene) of cloning vector pC194. The restriction map of pDN1822 is shown in FIG. 2, where the genes are indicated by arrows. The C-terminal part of amyQ on pDN1822 was then deleted by excision of a PvuI-PvuI fragment, which is shown hatched in FIG. 2, to obtain plasmid pDN1850 (FIG. 3). pDN1850 is amylase negative (Amy−) but harbors a N-terminal-part of amyQ and a C-terminal part of amyL. However, with a frequency of about $10^{-4}$, recombination between amyQ and amyL occurs resulting in the plasmids harbouring a hybrid QL amylase gene (amyQL+) and of an amylase positive phenotype (Amy+).

Figure 4:
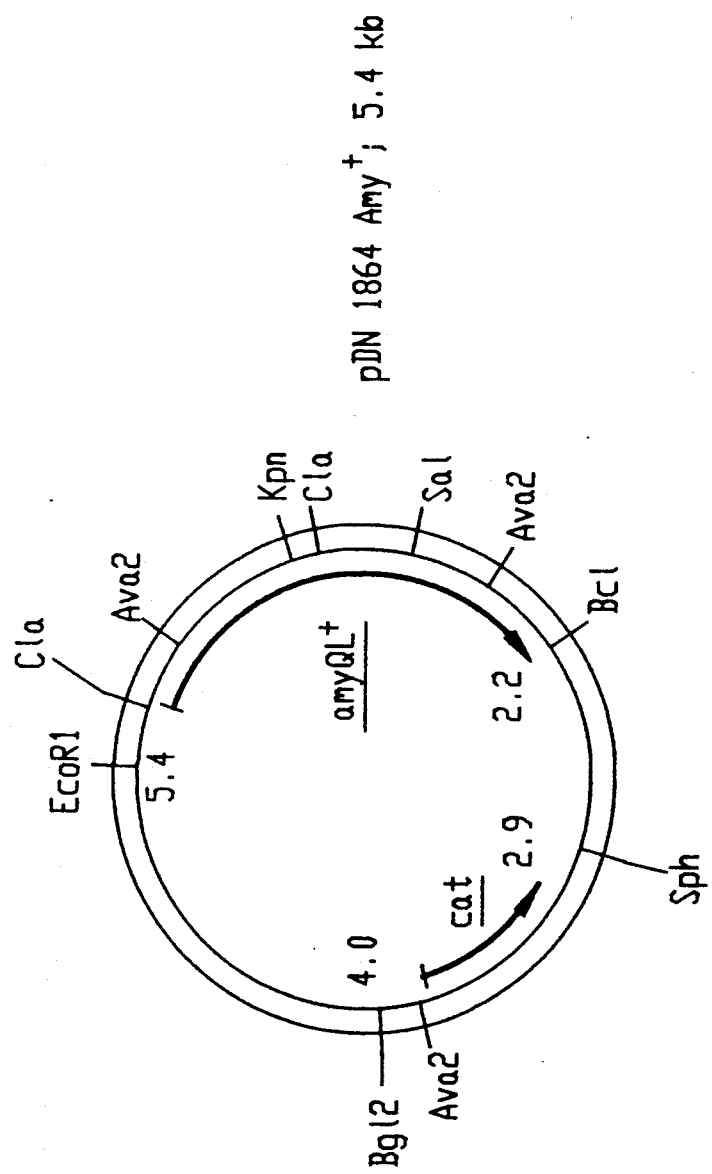
FIG. 4 shows the restriction map of plasmid pDN1864.

Transformation with a plasmid preparation of pDN1850 into a plasmid free *B. subtilis* recipient selecting for $Cam^R$ on starch containing agar plates resulted in about $1:10^4$ transformants producing an active amylase. These transformants were surrounded by a halo of degraded starch which could be identified by iodine vapor. These Amy+ transformants harbored a QL hybrid amylase gene on the plasmid. From these transformants the plasmids pDN1851 to pDN1865 were isolated, and it was found that transformants containing plasmids pDN1851, pDN1858 to pDN1862 and pDN1864 produced alpha-amylases that fulfill the objects of the invention. By restriction enzyme mapping of plasmid pDN1864, the amyQ L1864 gene was characterized (FIG. 4) and shown to harbor an AvaII site from amyQ, but not the nearby EcoRI site from amyQ. Hence, recombination between amyQ and amyL as indicated by the cross-hatched area in FIG. 3 took place between the codons coding for amino acid No. 58 and No. 67 in the *B. licheniformis* alpha-amylase. *B. subtilis* QL1864 is therefore producing a chimeric amylase composed of about 1/6 amyQ amylase at the N-terminal end and about 5/6 amyL amylase at the C-terminal end.

6.2 Analysis of Chimeric Amylase Produced by QL1864

In the following tests the enzyme units used are defined as indicated below:

One NU (NOVO Unit) of alpha-amylase activity is the amount of enzyme which breaks down 5.26 mg of dissolved starch per hour at 37° C., pH 5.6 and 0.0043 M of $Ca^{++}$ over a 7-20 minute reaction time.

One AG unit of glucoamylase activity is the amount of enzyme which hydrolyzes one micromole of maltose per minute at 25° C. and pH 4.3.

One pullulanase unit (PUN) is defined as the amount of enzyme which under standard conditions (temperature 40° C. and pH 5.0) hydrolyzes pullulan at a rate corresponding to the formation of reducing groups equivalent to 1 u/mole of glucose per minute.

6 2.1. Saccharification Test for Chimeric Amylase

As explained above it has been found that the presence of a residual B. licheniformis alpha-amylase activity originating from the liquefaction stage has a negative effect on maximum D-glucose yield in the saccharification stage when B. acidopullulyticus pullulanase and A. niger glucoamylase are used in combination.

In order to evaluate the influence of a residual activity from the chimeric alpha-amylases of the invention on the saccharification stage they were compared to the B. licheniformis alpha-amylase in the following way:

Substrates for saccharification were prepared by redissolving a DE 8 spray-dried maltodextrin (APS 840964A) in deionized water the making up to approximately 30% DS (dry substance). Saccharification experiments were carried out in standard 500 ml laboratory batch reactions.

pH's were measured at saccharification temperature with the pH electrode and pH meter calibrated and adjusted in buffer at 60° C.

| Substrate concentration | 28.2% (initial) 30.8% (final) |
|---|---|
| Temperature | 60° C. |
| pH (initial, at 60° C.) | 4.6 |
| Enzyme dosage: | |
| glucoamylase | 0.15 AG/g DS |
| pullulanase | 0.33 PUN/g DS |
| alpha-amylase | 60 NU/g DS |

The results of the tests are presented in Table I

TABLE I

SACCHARIFICATION TEST FOR CHIMERIC AMYLASE

| Alpha-Amylase | Reaction Conditions time (h) | pH | % DP$_1$ | % DP$_2$ | % DP$_3$ | % DP$_4$ |
|---|---|---|---|---|---|---|
| None | 24 | 4.5 | 92.8 | 2.5 | 1.1 | 3.6 |
| (Control) | 48 | 4.4 | 96.7 | 1.8 | 0.7 | 0.8 |
| | 72 | 4.4 | 96.8 | 2.0 | 0.6 | 0.6 |
| | 96 | 4.4 | 96.8 | 2.2 | 0.5 | 0.5 |
| B. licheniformis | 24 | 4.5 | 92.4 | 2.5 | 2.4 | 2.7 |
| | 48 | 4.5 | 95.9 | 1.8 | 1.5 | 0.9 |
| | 72 | 4.4 | 96.2 | 2.0 | 1.1 | 0.7 |
| | 96 | 4.4 | 96.4 | 2.1 | 0.9 | 0.6 |
| QL 1864 | 24 | 4.6 | 92.1 | 2.8 | 1.9 | 3.2 |
| | 48 | 4.5 | 96.3 | 1.7 | 1.2 | 0.9 |
| | 72 | 4.5 | 96.5 | 2.0 | 0.9 | 0.7 |
| | 96 | 4.5 | 96.6 | 2.1 | 0.8 | 0.6 |

From the results shown in Table I it is seen that although the presence of QL 1864 alpha-amylase slightly reduced the maximum obtainable DX (in comparison to the control), it represents a significant improvement over the B. licheniformis alpha-amylase.

6.2.2 Thermoactivation of Chimeric Amylase

In order to evaluate the thermoactivation of the chimeric alpha-amylases produced by the transformed strains the chimeric alpha-amylases were submitted to the following test:

| Substrate: | Phadebas tables (Phadebas ® amylase test, Pharmacia Diagnostics, Sweden) a cross-linked blue coloured starch polymer insoluble in water. |
|---|---|
| Buffer: | 0.1 M phosphate, pH 6.1, and TRIS buffer pH 9.5. |
| Enzyme: | alpha-Amylase diluted to 1–2 NU/ml in 0.09 M CaCl$_2$, pH 6.1. |
| Temperatures: | 37° C. and 85° C. |

1 ml alpha-amylase dilution was thoroughly mixed with 5 ml buffer and incubated in a water bath at the desired temperature prior to the addition of one Phadebas table.

The test tube was shaken for 15 seconds on a whirl mixer before it is placed in the water bath again.

After exactly 15 minutes the reaction was stopped by the addition of 1 ml 1 M NaOH. After mixing the mixture was filtered through a 9 cm Whatman ® GF/A of FG/C filter.

The optical density of the filtrate was measured at a wavelength of 620 nm, and was found to be linearly related to the activity of alpha-amylase added.

The results are presented in Table II below together with values from tests with pure B. licheniformis and B. amyloliquefaciens alpha-amylases.

TABLE II

THERMOACTIVATION OF CHIMERIC AMYLASE

| Alpha-Amylase | Phadebas 37° C. pH 6.1:pH 9.5 | Phadebas pH 6.1 75° C.:37° C. |
|---|---|---|
| B. licheniformis (control) | 0.4 | 3.7 |
| QL 1864 | 2.5 | 2.5 |
| QL 1861 | 2.2 | 2.2 |
| QL 1851 | 2.1 | 2.1 |
| QL 1862 | 2.0 | 2.0 |
| QL 1858 | 2.0 | 2.0 |
| B. amyloliquefaciens (control) | 8.7 | 0.01 |

The data presented in Table II demonstrate that the chimeric alpha-amylases of the invention are as thermoactivated as the B. licheniformis alpha-amylase, and less sensitive to alkaline pH than the B. amyloliquefaciens alpha-amylase.

6.2.3. Thermostability of Chimeric Amylase

In order to evaluate the stability of the alphaamylases of the invention the following steel tube tests were performed:

A DE 7 maltodextrin redissolved in deionized water was used as substrate under the following conditions:

| Substrate: | 32–33 percent |
|---|---|
| alpha-amylase dosage: | 120 NU/g maltodextrin |
| Temperature: | 105° C. |
| pH: | 5.5 |
| Calcium content: | 60 ppm |

In each test 5 steel tubes containing the above reaction mixture were placed in an oil bath at 105° C. and taken out after 10, 20, 30, 40, and 60 minutes, respectively, and the residual alpha-amylase activity measured by the Phadebas method described above. The half life, $T_{\frac{1}{2}}$, is calculated by linear repression of log (residual activity) versus time. The results are shown in Table III below:

TABLE III

THERMOSTABILITY OF CHIMERIC AMYLASES

| Alpha-Amylase | $T_{\frac{1}{2}}$ minutes |
|---|---|
| B. amyloliquefaciens (control) | 5 |
| QL 1851 | 22 |
| QL 1858 | 25 |
| QL 1861 | 18 |
| QL 1862 | 22 |
| QL 1864 | 24 |
| B. licheniformis (control) | 23 |

From the results shown in Table III it is clearly seen that the hybrid alpha-amylases of the invention have retained the stability of the B. licheniformis alpha-amylase.

The present invention is not to be limited in scope by the microorganisms and chimeric enzymes exemplified since these are intended as a single illustration of one aspect of the invention and any microorganisms or chimeric enzyme which are functionally equivalent are within the scope of this invention. Indeed various modifications of the invention in addition to those shown and described herein will become apparent to those skilled in the art from the foregoing description and accompany drawings. Such modifications are intended to fall within the scope of the appended claims.

What is claimed is:

1. A chimeric alpha-amylase that (i) comprises the general formula I $$Q-R-L \qquad (I)$$

in which

Q comprises a N-terminal polypeptide of about 55 to 60 amino acid residues which is at least 75% homologous to the 55 N-terminal amino acid residues in the *Bacillus amyloliquefaciens* alpha-amylase as described in FIG. 5:

R comprises a polypeptide of the general formula Ia $$\begin{array}{c} [58] \quad [60] \\ \text{Pro—Tyr—Asp—Leu—Tyr—Asp—Leu—Gly—} \\ [70] \\ \text{Glu—Phe—X}_8\text{—Gln—Lys—Gly—Thr—Val—Arg—} \\ [80] \\ \text{Thr—Lys—Tyr—Gly—Thr—Lys—X}_9\text{—Glu—Leu—} \end{array} \qquad (Ia)$$

-continued $$\text{Gln—X}_{10}\text{—Ala—Ile—Lys} \qquad [88]$$

in which $X_8$ consists of His or Gln, $X_9$ consists of Gly or Ser, $X_{10}$ consists of Ser or Asp, and L comprises a C-terminal polypeptide of from 390 to 400 amino acid residues which is at least 75% homologous to the 395 C-terminal amino acid residues in the *Bacillus licheniformis* 584 (ATCC 17811) alpha-amylase, and that (ii) exhibits greater thermal stability then *Bacillus amyloliquefaciens* alpha-amylase.

2. The chimeric alpha-amylase according to claim 1, in which $X_8$ consists of His, $X_9$ consists of Gly, and $X_{10}$ consists of Ser.

3. The chimeric alpha-amylase according to claim 1, in which $X_8$ consists of Gln, $X_9$ consists of Ser, and $X_{10}$ consists of Asp.

4. The chimeric alpha-amylase according to claim 1, in which the homologies are at least 80 percent.

5. The chimeric alpha-amylase according to claim 1, in which the homologies are at least 90 percent.

6. The chimeric alpha-amylase according to claim 1, in which Q comprises an N-terminal polypeptide residue of the general formula Ib $$\begin{array}{c} [5] \quad [10] \quad [15] \\ X_1\text{—Asn—Gly—Thr—Leu—Met—Gln—Tyr—Phe—Glu—Trp—Tyr—X}_2\text{—Pro—Asn—Asp—} \\ [20] \quad [25] \quad [30] \quad [35] \\ \text{Gly—Gln—His—Trp—Lys—Arg—Leu—Gln—Asn—Asp—X}_3\text{—Leu—X}_4\text{—Gly—Ile—Thr—} \\ [40] \quad [45] \quad [50] \\ \text{Ala—Val—Trp—Ile—Pro—Pro—Ala—Tyr—Lys—Gly—X}_5\text{—Ser—Gln—X}_6\text{—Asp—X}_7\text{—} \\ [55] \\ \text{Gly—Tyr—Gly;} \end{array} \qquad (Ib)$$

in which $X_1$ consists of Ala-Asn-Leu or Val, $X_2$ consists of Met or Thr, $X_3$ consists of Ser-Ala-Tyr or Ala-Glu-His, $X_4$ consists of Ala-Gly-His or Ser-Asp-ILe, $X_5$ consists of Thr or Leu, $X_6$ consists of Ala or Ser, and $X_7$ consists of Val or Asn.

7. The chimeric alpha-amylase according to claim 6, in which $X_1$ consists of Val, $X_2$ consists of Thr, $X_3$ consists of Ala-Glu-His, $X_4$ consists of Ser-Asp-Ile, $X_5$ consists of Leu, $X_6$ consists of Ser, and $X_7$ consists of Asn.

8. The lapha-amylase according to claim 4, 5, 6, or 7, in which L comprises a C-terminal polypeptide residue of the general formula Ic $$\begin{array}{c} [90] \quad [95] \quad [100] \\ \text{Ser—Leu—His—Ser—Arg—Asp—Ile—Asn—Val—Tyr—Gly—Asp—Val—} \end{array} \qquad (Ic)$$

[105]                          [110]                            [115]
Val—Ile—Asn—His—Lys—Gly—Gly—Ala—Asp—Ala—Thr—Glu—Asp—Val—Thr—

[120]                          [125]                            [130]
Ala—Val—Glu—Val—Asp—Pro—Ala—Asp—Arg—Asn—Arg—Val—Ile—Ser—Gly—

[135]                          [140]                            [145]
Glu—His—Arg—Ile—Lys—Ala—Trp—Thr—His—Phe—His—Phe—Pro—Gly—Arg—

[150]                          [155]                            [160]
Gly—Ser—Thr—Tyr—Ser—Asp—Phe—Lys—Trp—His—Trp—Tyr—His—Phe—Asp—

[165]                          [170]                            [175]
Gly—Thr—Asp—Trp—Asp—Glu—Ser—Arg—Lys—Leu—Asn—Arg—Ile—Tyr—Lys—

[180]                          [185]                            [190]
Phe—Gln—Gly—Lys—Ala—Trp—Asp—Trp—Glu—Val—Ser—Asn—Glu—Asn—Gly—

[195]                          [200]                            [205]
Asn—Tyr—Asp—Tyr—Leu—Met—Tyr—Ala—Asp—Ile—Asp—Tyr—Asp—His—Pro—

[210]                          [215]                            [220]
Asp—Val—Ala—Ala—Glu—Ile—Lys—Arg—Trp—Gly—Thr—Trp—Tyr—Ala—Asn—

[225]                          [230]                            [235]
Glu—Leu—Gln—Leu—Asp—Gly—Phe—Arg—Leu—Asp—Ala—Val—Lys—His—Ile—

[240]                          [245]                            [250]
Lys—Phe—Ser—Phe—Leu—Arg—Asp—Trp—Val—Asn—His—Val—Arg—Glu—Lys—

[255]                          [260]                            [265]
Thr—Gly—Lys—Glu—Met—Phe—Thr—Val—Ala—Glu—Tyr—Trp—Gln—Asn—Asp—

[270]                          [275]                            [280]
Leu—Gly—Ala—Leu—Glu—Asn—Tyr—Leu—Asn—Lys—Thr—Asn—Phe—Asn—His—

[285]                          [290]                            [295]
Ser—Val—Phe—Asp—Val—Pro—Leu—His—Tyr—Gln—Phe—His—Ala—Ala—Ser—

[300]                          [305]                            [310]
Thr—Gln—Gly—Gly—Gly—Tyr—Asp—Met—Arg—Lys—Leu—Leu—Asn—Ser—Thr—

[315]                          [320]                            [325]
Val—Val—Ser—Lys—His—Pro—Leu—Lys—Ala—Val—Thr—Phe—Val—Asp—Asn—

[330]                          [335]                            [340]
His—Asp—Thr—Gln—Pro—Gly—Gln—Ser—Leu—Glu—Ser—Thr—Val—Gln—Thr—

[345]                          [350]                            [355]
Trp—Phe—Lys—Pro—Leu—Ala—Tyr—Ala—Phe—Ile—Leu—Thr—Arg—Glu—Ser—

[360]                          [365]                            [370]
Gly—Tyr—Pro—Gln—Val—Phe—Tyr—Gly—Asp—Met—Tyr—Gly—Thr—Lys—Gly—

[375]                          [380]                            [385]
Asp—Ser—Gln—Arg—Glu—Ile—Pro—Ala—Leu—Lys—His—Lys—Ile—Glu—Pro—

[390]                          [395]                            [400]
Ile—Leu—Lys—Ala—Arg—Lys—Gln—Tyr—Ala—Tyr—Gly—Ala—Gln—His—Asp—

[405]                          [410]                            [415]
Tyr—Phe—Asp—His—His—Asp—Ile—Val—Gly—Trp—Thr—Arg—Glu—Gly—Asp—

[420]                          [425]                            [430]
Ser—Ser—Val—Ala—Asn—Ser—Gly—Leu—Ala—Ala—Leu—Ile—Thr—Asp—Gly—

[435]                          [440]                            [445]
Pro—Gly—Gly—Ala—Lys—Arg—Met—Tyr—Val—Gly—Arg—Gln—Asn—Ala—Gly—

[450]                          [455]                            [460]
Glu—Thr—Trp—His—Asp—Ile—Thr—Gly—Asn—Arg—Ser—Glu—Pro—Val—Val—

[465]                          [470]                            [475]
Ile—Asn—Ser—Glu—Gly—Trp—Gly—Glu—Phe—His—Val—Asn—Gly—Gly—Ser—

[480] [483]
Val—Ser—Ile—Tyr—Val—Gln—Arg .

9. A process for converting starch into high dextrose syrup, comprising:
   (a) reacting the starch with the chimeric alpha-amylase of claim 1, 2, 3, 4, 5, 6, or 7 to form oligosaccharides; and
   (b) reacting the oligosaccharides formed in step (a) with a glucoamylase to form dextrose.

10. A process for converting starch into high dextrose syrup, comprising:
    (a) reacting the starch with the chimeric alpha-amylase of claim 8 to form oligosaccharides; and
    (b) reacting the oligosaccharides formed in step (a) with a glucoamylase to form dextrose.

* * * * *